(12) United States Patent
Kunz

(10) Patent No.: US 6,239,428 B1
(45) Date of Patent: May 29, 2001

(54) ION MOBILITY SPECTROMETERS AND METHODS

(75) Inventor: Roderick R. Kunz, Acton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/517,041

(22) Filed: Mar. 2, 2000

Related U.S. Application Data
(60) Provisional application No. 60/122,774, filed on Mar. 3, 1999.

(51) Int. Cl.[7] .................................................... H01J 49/40
(52) U.S. Cl. ............................................ 250/287; 250/282
(58) Field of Search ..................................... 250/287, 282

(56) References Cited

U.S. PATENT DOCUMENTS

| | | | |
|---|---|---|---|
| 4,445,038 | 4/1984 | Spangler et al. | 250/287 |
| 5,338,931 | 8/1994 | Spangler et al. | 250/287 |
| 5,394,413 | 2/1995 | Zayhowski | 372/10 |
| 5,587,581 | 12/1996 | Stroosnyder | 250/287 |

FOREIGN PATENT DOCUMENTS

| | | |
|---|---|---|
| 196 09 581 C1 | 12/1996 | (DE) . |
| 196 09 582 | 12/1996 | (DE) . |

OTHER PUBLICATIONS

J.A. Herman et al., "Energy Dependence of the Fragmentation of $C_6H_{12}^{30}$ Ions" Org. Mass. Spectrom., 17, 143 (1982).

J. J. Zayhowski et al. "Diode–Pumped Passively Q–Switched Picosecond Microchip Lasers" Opt. Lett., 19, 1427 (1994).

P. Becotte–Haigh et al., "Performance and Applications Of A New Portable Detection System For Drugs and Explosives", Proceedings of the $6^{th}$ Int. Conf. On Ion Mobility Spectrometry, Aug., 1997.

G.A. Eiceman and Z. Karpas "Ion Mobility Spectrometry" CRC Press, Boca Raton, FL, 1994, pp. 19–43.

G. A. Eiceman et al. "Quantitative Assessment of a Corona Discharge Ion Source in Atmospheric Pressure Ionization––Mass Spectrometry for ambient Air Monitoring" Int. J. Environ. Chem., 33, 161 (1988).

D.M. Lubman and M.N. Kronick "Resonance–Enhanced Two–Photon Ionization Spectroscopy in Plasma Chromatography" Anal Chem, 55, 1486 (1983).

W. McGann et al. "A New, High Efficiency Ion Trap Mobility Detection System for Narcotics and Explosives", Proc. SPIE 2092, 64 (1993).

(List continued on next page.)

Primary Examiner—Jack Berman
(74) Attorney, Agent, or Firm—Fish & Richardson P.C.

(57) ABSTRACT

Ion mobility spectrometer systems and methods of using such systems are disclosed. The systems and methods can combine two different ionization techniques (e.g., proton affinity ionization and electron transfer ionization) to provide enhanced detection sensitivity and/or detection selectivity of certain target compounds.

37 Claims, 16 Drawing Sheets

OTHER PUBLICATIONS

L. Kolaitis et al. "Atmospheric Pressure Ionizatrion Mass Spectrometry with Laser–Produced Ions" Anal Chem., 58, 1993 (1986).

J.W. Leonhardt et. al "Determination of Benzene, Toluene and Xylene by Means of an Ion Mobility Spectrometer Device Using Photoionization" Proceedings of the $3^{rd}$ International Workshop on Ion Mobility Spectrometry, J. Cross, ed., Lyndon Johnson Space Center, Houston, Report S–799, 49–56 (1995).

A.G. Harrison "Chemical Ionization Mass Spectrometryz" CRC Press, Boca Raton, FL, 1992, 12–15.

C. S. Leasure et al. "Photoionization in Air with Ion Mobility Spectrometry Using a Hydrogen Discharge Lamp" Anal. Chem., 58, 2142 (1986).

W.J. Simonsick, Jr., and R.A. Hites "Characterization of High Molecular Weight Polycyclic Aromatic Hydrocarbons by Charge Exchange Chemical Ionization Mass Spectrometry" Anal. Chem., 58, 2114 (1986).

M.A. Baim et al. "Ion Mobility detector for Gas Chromatography with a Direct Photoinonization Source" Anal Chem., 55, 1761 (1983).

J.J. Zayhowski "Microchip lasers create light in small spaces" Laser Focus World, Apr. 1996.

ION MOBILITY SPECTROMETERS AND METHODS

CROSS-REFERENCE TO RELATED APPLICATION

This application claims priority under 35 U.S.C. §119(e)(1) to U.S. patent application Ser. No. 60/122,774, filed Mar. 3, 1999, and entitled "Detection of Contraband Via Laser Ionization-Chemical Ionization Ion Mobility Spectroscopy Using A 30-Kilowatt Microchip Ultraviolet Laser", which is hereby incorporated by reference in its entirety.

This invention was made with government support under Contract No. F19628-95C-0002 awarded by the Air Force. The government has certain rights in the invention.

FIELD OF THE INVENTION

The invention relates to ion mobility spectrometers and methods.

BACKGROUND OF THE INVENTION

Ion mobility spectrometers are commonly used to detect the presence of target compounds. Typically, in an ion mobility spectrometer a target compound is ionized, passed through an electric field and then detected by an electrode detector.

The target compound can be directly ionized by an ionization source that emits energy that interacts with and ionizes the target compound. Alternatively or additionally, the target compound can be indirectly ionized by an ionization source which emits energy that interacts with and ionizes an intermediate compound which, in turn, interacts with and ionizes the target compound.

The amount of time it takes for the ionized target compound to pass through the electric field and reach the electrode detector can depend on a number of parameters, including the mass of the ionized target compound, the charge of the ionized target compound, and the strength of the electric field. By manipulating these parameters, the ionized target compound can be detected by measuring the ion current at the electrode detector at a predetermined time.

One type of ion mobility spectrometer is based on proton transfer. In this type of spectrometer, an ionized intermediate compound transfers a proton to the target compound to form the ionized target compound, which is then passed through an electric field and detected. Generally, the proton affinity of the intermediate compound is less than the proton affinity of the target compound.

Another type of ion mobility spectrometer is based on electron transfer. In this type of spectrometer, an ionized intermediate compound transfers an electron to the target compound to form the ionized target compound, which is then passed through an electric field and detected. Usually, the ionization potential of the intermediate compound is greater than the ionization potential of the target compound.

SUMMARY

In one aspect, the invention features a method of detecting a target compound in a sample. The method includes subjecting the sample to conditions sufficient to ionize the target compound by proton transfer ionization, and subjecting the sample to conditions sufficient to ionize the target compound by electron transfer ionization. The method also includes detecting the proton transfer first ionized sample by ion mobility spectrometry, and detecting the electron transfer ionized sample by ion mobility spectrometry.

Embodiments can include one or more of the following features.

The method can include comparing the detection of the proton transfer ionized sample and the detection of the electron transfer ionized sample. In some embodiments, the method includes determining the presence of the target compound by detection of the compound by both proton transfer ionization and electron transfer ionization.

The sample can be obtained by vapor collection.

The target compound can have a proton affinity of about 7.5 eV or greater and/or an ionization potential of about 10 eV or less. For example, the target compound can have a proton affinity of from about 9 eV to about 12 eV and/or an ionization potential of from about 5 eV to about 8 eV. In some embodiments, the target compound can be an organonitrogen compound. In certain embodiments, the target compound is at least one of LSD, heroin, cocaine, or their derivatives.

The proton transfer ionization can include forming a first ionized intermediate compound capable of transferring a proton from the first ionized intermediate compound to the target compound.

The electron transfer ionization can include forming a second ionized intermediate compound capable of transferring an electron from the second ionized intermediate compound to the target compound.

The method can include using a first and/or second intermediate compound. The first intermediate compound can be capable of ionizing a first set of compounds including the target compound and other known compounds, and the second intermediate compound can be capable of ionizing a second set of compounds including the target compound and other known compounds, which can be different than the first set. The first intermediate compound can be an amine, such as a primary amine. The second intermediate compound can be an aromatic compound and/or a compound containing a benzene ring.

The proton transfer and electron transfer ionizations can be detected simultaneously, or the proton transfer and electron transfer ionizations can be detected in series.

In another aspect, the invention features a system capable of detecting a target compound. The system includes a proton transfer ionization source capable of ionizing a first intermediate compound to form a first ionized intermediate compound, an electron transfer ionization source capable of ionizing a second intermediate compound to form a second ionized intermediate compound, and a detector capable of detecting the target compound after ionization by electron transfer or proton transfer. The first intermediate compound can have a lower proton affinity than the target compound, and the second intermediate compound can have a higher ionization potential than the target compound.

Embodiments can have one or more of the following features.

The detector can be an ion mobility spectrometer. The detector can be two ion mobility spectrometers operating in parallel. The detector can be a single ion mobility spectrometer for alternately detecting the proton transfer source and the electron transfer source.

The system can further include a comparison apparatus in electrical communication with the detector. The comparison apparatus can compare a first signal from ionization by proton transfer ionization with a second signal from ionization by electron transfer ionization. The comparison apparatus can determine the presence of the target compound by detection of the compound in both the first and second signals.

The first ionization source can emit electrons capable of ionizing the first intermediate compound to form the first ionized intermediate compound. The second ionization source can be a laser, such as a laser that can emit photons having a wavelength of at least about 190 nanometers, a microchip UV laser, and/or a tunable laser.

The target compound can have a proton affinity of about 7.5 eV or greater and/or an ionization potential of about 10 eV or less. For example, the target compound can have a proton affinity of from about 9 eV to about 12 eV and/or an ionization potential of from about 5 eV to about 8 eV. In some embodiments, the target compound can be an organonitrogen compound. In certain embodiments, the target compound is at least one of LSD, heroin, cocaine, or their derivatives.

In a further embodiment, the invention features a system for detecting a target compound in a sample that includes a sample inlet, a first ionization source that can emit electrons capable of ionizing a first intermediate compound to form a first ionized intermediate compound, a laser that can emit photons capable of ionizing a second intermediate compound to form a second ionized intermediate compound, a detector that includes an ion mobility spectrometer capable of detecting the first ionized target compound and the second ionized target compound, and a comparison apparatus in electrical communication with the detector so that the comparison apparatus can compare a first signal corresponding to the first ionized target compound and a second signal corresponding to the second ionized target compound. The first intermediate compound can have a lower proton affinity than the target compound, and the target compound can have a proton affinity of about 7.5 eV or greater. The ionization potential of the second intermediate compound can be greater than an ionization potential of the target compound, and the target compound can have an ionization potential of about 10 eV or less.

Embodiments can have one or more of the following features.

The photons can have a wavelength of at least about 190 nanometers.

The laser can be a UV microchip laser and/or a tunable laser.

The detector can be two ion mobility spectrometers operating in parallel.

In one aspect, the invention relates to the appreciation that ion mobility spectrometer systems and methods that compare the target compound output signals from more than one type of ion mobility spectrometer can provide enhanced detection sensitivity and/or detection selectivity for the target compound relative to ion mobility spectrometer systems and methods that involve only one type ion mobility spectrometer. The systems can include a single ion mobility drift tube equipped with two different ionization sources (e.g., a laser and a corona source). Alternatively or additionally, the systems can include two different drift tubes, ionization sources and/or gas streams.

In certain embodiments, the system is in the form of a portable device that includes a vacuum unit for taking in the sample compound(s) to be analyzed. The device can be lightweight and/or portable. The device can, for example, be used to detect the presence or absence of target compound(s) in samples at locations remote from a laboratory (e.g, airports, bus stations, and/or ships).

In embodiments, the invention relates in part to the appreciation that for certain compounds there is a lack of an inverse relationship between ionization potential and proton affinity. For these compounds, combining ion mobility spectrometer systems and/or methods based on proton affinity and electron transfer can enhance detection selectivity and/or sensitivity.

Embodiments can have one or more of the following advantages.

The systems and/or methods of the invention can result in increased sensitivity and/or selectivity for detection of certain compounds, including some contraband compounds. The systems of the invention can be relatively easy to use, small, lightweight and/or portable.

Other advantages and features of the invention will be understood from the figures, detailed description and claims.

DETAILED DESCRIPTION

Figure 1:
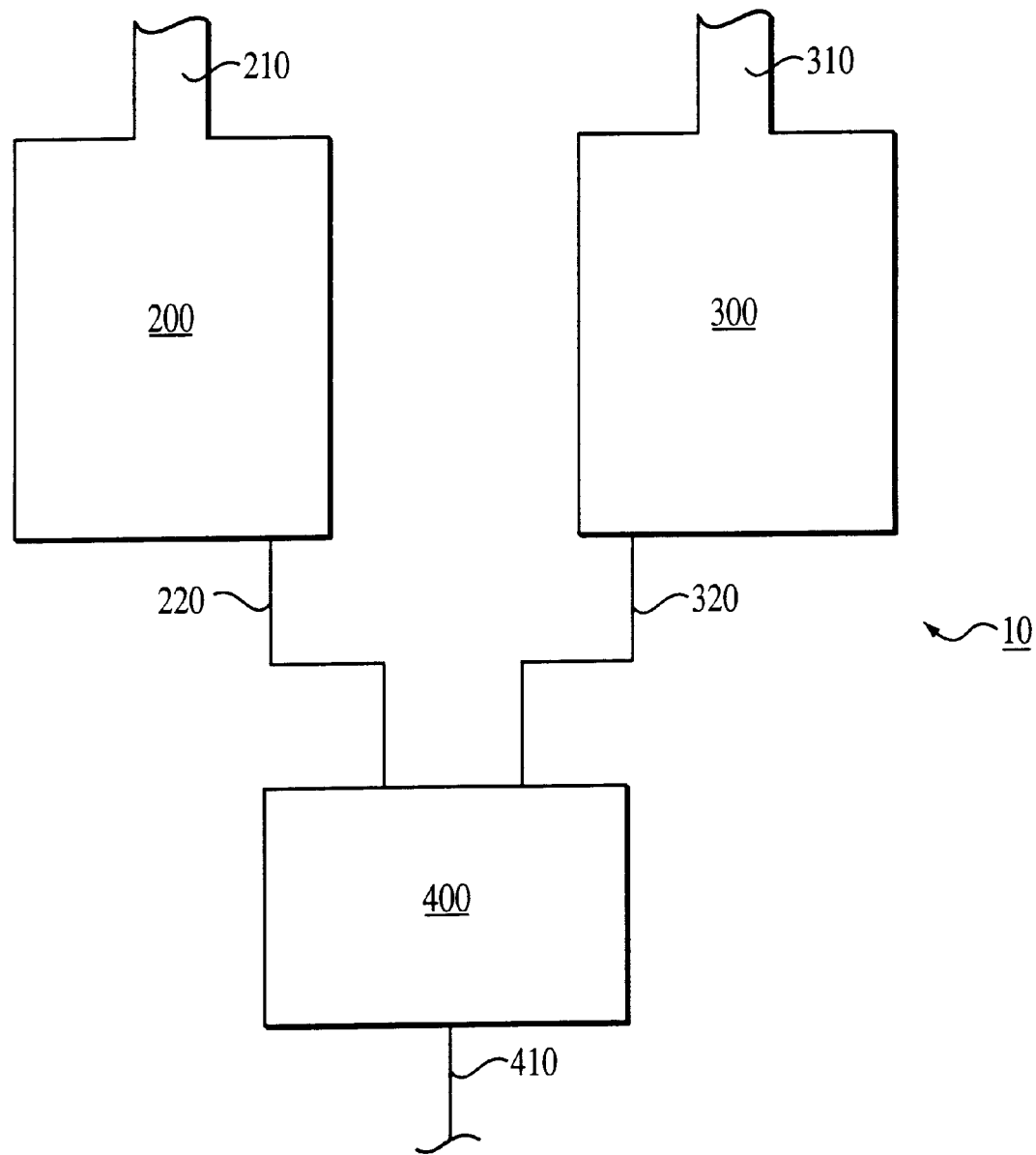
FIG. 1 is a schematic representation of an ion mobility spectrometer system according to an embodiment of the invention.

Referring to FIG. 1, a combined proton affinity ionization-electron potential ionization system 10 includes a pair of ion mobility spectrometers 200, 300, and a comparison apparatus 400. Spectrometer 200 effects ionization by one mechanism, such as proton affinity ionization, and spectrometer 300 effects ionization by another mechanism, such as electron potential ionization. Each spectrometer has an inlet 210, 310 for receiving an aliquot of the same sample. The sample may be obtained by drawing a vacuum near a suspect object, such as, e.g., a suitcase, a handbag or the like. Comparison apparatus 400 analyzes the data from spectrometers 200 and 300 to determine whether a target compound, e.g., a contraband compound, is present in the sample.

Figure 2:
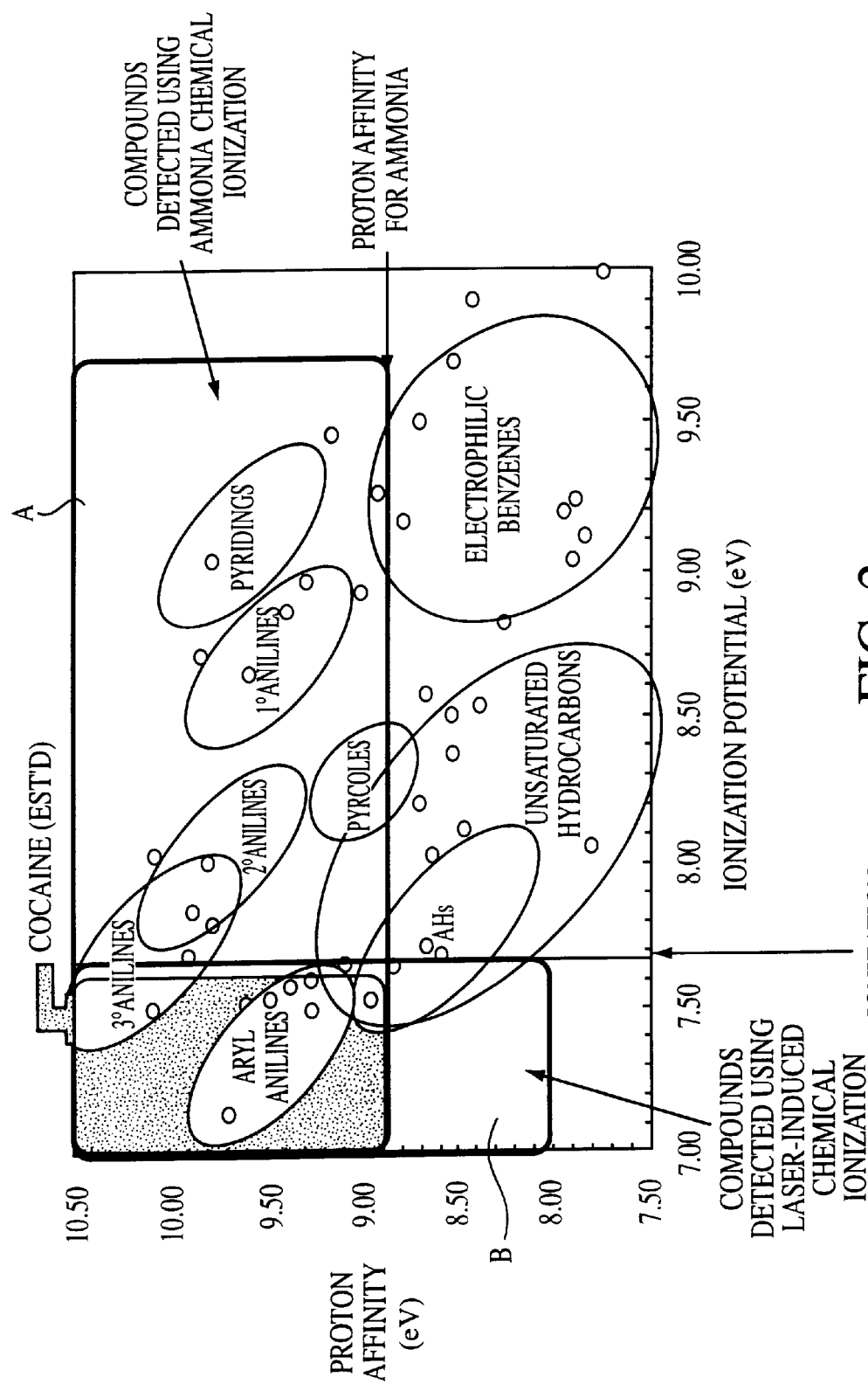
FIG. 2 is a plot of proton affinity and ionization potential for certain target compounds.

Referring as well to FIG. 2, the sensitivity and discrimination of the detection of a target compound can be enhanced by operating system 10 to take advantage of the property that the ionization potential and proton affinity do not have a predictable inverse relationship in the regime including many contraband compounds. For example, compounds having a proton affinity of about 7.5 eV or greater (e.g., about 9 eV or greater, such as from about 9 eV to about 12) and an ionization potential of about 10 eV or less (e.g., about 8 eV or less, such as from about 5 eV to about 8 eV) include many contraband compounds, such as organo-nitrogen compounds, including, for example, THC, LSD, heroin, cocaine and their byproducts. Other contraband compounds falling within the aforementioned ranges of ionization potential and proton affinity are disclosed, for example, in P. Becotte-Haigh et al., *Performance and Applications of a New Portable Detection System for Drugs and Explosives,* proceedings at the 6$^{th}$ Int. Conf. On Ion Mobility Spectrometry, August, 1997, which is hereby incorporated by reference. Without wishing to be bound by theory, it is believed that, for at least some of these compounds complex molecular rearrangements and resonance-structure stabilization effects may result in the variance from the general inverse relationship between proton affinity and ionization potential. The measurement of the ionization potential of a compound is described, for example, in R. D. Levin and S. G. Lias, National Bureau of Standards Report No. NSRDS-NBS 71, October 1982, which is hereby incorporated by reference. The measurement of the proton affinity of a compound is described, for example, in S. G. Lias et al., J. Phys. Chem. Ref. Data 13, 695 (1984), which is hereby incorporated by reference. The data represented in FIG. 2 is disclosed in these two references.

Discrimination and sensitivity can be enhanced by making both ionization potential and proton affinity measurements. For example, an interfering gas, R, may have a proton affinity higher than a particular target compound, which may reduce the discrimination of the detector by interfering with the signal of the target compound. As shown in FIG. 2, using ammonia as an intermediate compound in proton affinity ionization, depicted by box A, a variety of compounds might be ionized along with the target compound, cocaine. However, the ionization potentials of these compounds vary widely. A reactive gas, G, that can form positive ions through interaction with photons can be used as an intermediate compound for electron transfer ionization to ionize, for example, compounds in box B. As evident, in this case, electron transfer ionization under these conditions results in ionization of fewer compounds, which simplifies the spectrum, enhancing sensitivities. A positive identification may be made on the basis of the simpler spectrum. Alternatively, or in addition, the confidence of the identification of a target compound is enhanced by comparing the data from both spectrometers to determine whether the compound has been detected by both techniques.

Referring back to FIG. 1, an ion mobility spectrometer system 10 according to one embodiment of the invention includes ion mobility spectrometers 200 and 300, and a comparison apparatus 400. Spectrometers 200 and 300 have gas inlets 210 and 310, respectively (e.g., each for a target compound and an appropriate intermediate compound). Spectrometers 200 and 300 also have signal outputs 220 and 320, respectively (e.g., corresponding to the ionized target compound formed in spectrometers 200 and 300, respectively). Outputs 220 and 320 are in electrical communication with comparison apparatus 400. Comparison apparatus 400 compares signals 220 and 320 and outputs this comparison as an output signal 410.

Spectrometer 200 is designed to ionize the target compound via a first ionization mechanism, and spectrometer 300 is designed to ionize the target compound via a different ionization mechanism. The ionization of the target compound in spectrometer 200 can occur directly and/or indirectly. Similarly, the ionization of the target compound in spectrometer 300 can occur directly and/or indirectly. In certain embodiments, the target compound is ionized in spectrometer 200 via a proton transfer mechanism using an appropriate intermediate compound, and the target compound is ionized in spectrometer 300 via an electron transfer mechanism using an appropriate intermediate compound.

Examples of proton affinity ion mobility spectrometers are disclosed, for example, in G. A. Eiceman and Z. Karpas, *Ion Mobility Spectrometry,* CRC Press, Boca Raton, Fla., 1994, p. 19; G. A. Eiceman, *Quantitative Assessment f a Corona Discharge Ion Source in Atmospheric Pressure Ionization-Mass Spectrometry for Ambient Air Monitoring,* Int. J. Environ. Anal. Chem., 33, 161 (1988); and P. Becotte-Haigh et al., *Performance and Applications of a New Portable Detection System for Drugs and Explosives,* proceedings at the 6$^{th}$ Int. Conf. On Ion Mobility Spectrometry, August, 1997, which are hereby incorporated by reference. In one embodiment, spectrometer 200 is a commercially available proton affinity ion mobility spectrometer sold under the tradename Mark II by Ion Track Instruments, located in Wilmington, Mass.

Examples of electron transfer ion mobility spectrometers are disclosed for example, in Alex G. Harrison, *Chemical Ionization Mass Spectrometry,* CRC Press, Boca Raton, Fla., 1992, p. 12; W. J. Simonsick, Jr. and R. A. Hites, *Characterization of High Molecular Weight Polycyclic Aromatic Hydrocarbons by Charge Exchange Chemical Ionization Mass Spectrometry,* Anal. Chem., 58, 2114 (1986); J. A. Herman et al., *Energy Dependence of the Fragmentation of Some $C_6H_2^+$ Ions,* Org. Mass. Spectrom., 17, 143 (1982); C. S. Leasure et al., *Photoionization in Air with Ion Mobility Spectrometry Using a Hydrogen Discharge Lamp,* Anal. Chem., 58, 2142 (1986); M. A. Baim et al., *Ion Mobility Detector for Gas Chromatography with a Direct Photoionization Source,* Anal. Chem., 55 1761 (1983), which are hereby incorporated by reference. In one embodiment, spectrometer 300 is a modified version of the above-mentioned Mark II spectrometer (Ion Track Systems, Wilimington, Mass.) in which the $^{63}$Ni source is replaced with the 266 nanometer microchip UV laser and mirror cavity described in U.S. Pat. No. 5,394,413 to Zayhowski, which is hereby incorporated by reference.

Comparison apparatus 400 can be any apparatus capable of comparing signals 220 and 320 and providing an output signal 410 of the compared signals. In certain embodiments, signal 410 represents a positive output for the target compound only if each of signals 220 and 320 represents a positive output for the target compound. The signal from detector 220 at a given time can be used as an X-axis coordinate and the signal from detector 320 at the same time can be used as a Y-axis coordinate, thereby creating a two dimensional image for each time in signals 220 and 320. In some embodiments, comparison apparatus 400 is a computer, and the comparison of signals 220 and 320 is performed with commercially available software, such as, for example, LabView®, commercially available from National Instruments, and Matlab, commercially available from The MathWorks, Incorporated. In some embodiments, the detection algorithm can analyze signals 220 and 320 relative to an unknown.

Figure 3:
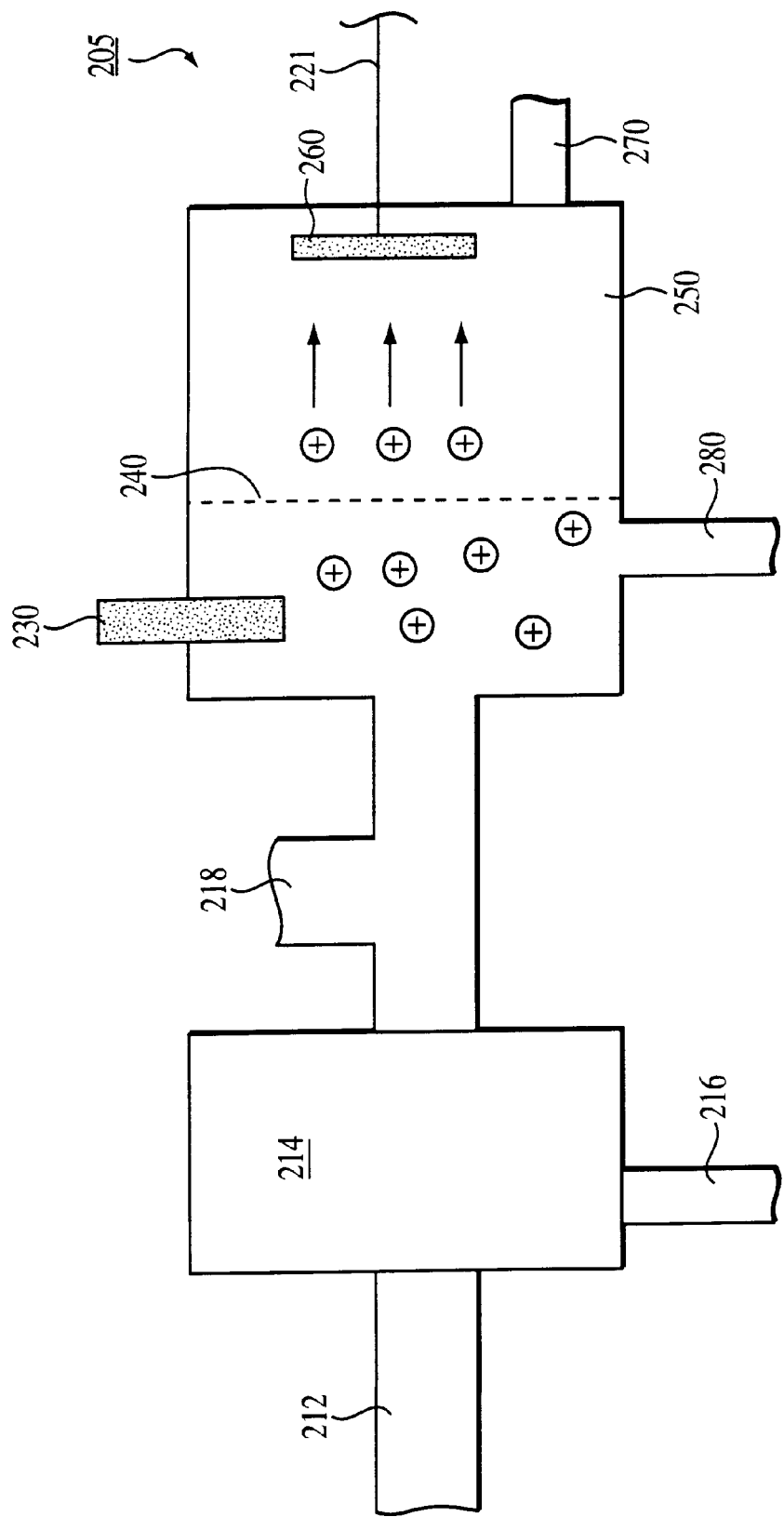
FIG. 3 is a cross-sectional view of a proton affinity ion mobility spectrometer according to one embodiment of the invention.

FIG. 3 is a cross-sectional view of an embodiment of a proton affinity ion mobility spectrometer 205. A gas containing the target compound enters through port 212 and flows toward ionizer 230. Prior to reaching ionizer 230, the gas interacts with preconcentrator 214 which can condense relatively high boiling point species (e.g., the target compound) contained in the gas. The noncondensed, relatively low boiling point species exit through output 216. The portion of the gas that is condensed by preconcentrator 214 (e.g., the target compound) is re-vaporized and mixed with an appropriate intermediate compound that enters spectrometer 205 through port 218. The gas mixture containing the target compound and the intermediate compound interacts with ionizer 230 which ionizes the intermediate compound. The ionized intermediate compound, in turn, interacts with and ionizes the target compound by proton transfer (e.g., by collisions between the ionized intermediate compound and the target compound). The ionized target compound is attracted to a grid 240 and subsequently flows through a drift region 250 toward an electrode detector 260. The ion current at electrode detector 260 is measured as a function of time and output as signal 221.

The target compound can be any compound capable of being ionized by an electron transfer process using an appropriate intermediate compound. In some embodiments, the target compound has a proton affinity of about 7.5 eV or greater (e.g., about 9 eV or greater, such as from about 9 eV to about 12) and an ionization potential of about 10 eV or less (e.g., about 8 eV or less, such as from about 5 eV to about 8 eV). Examples of such target compounds include certain contraband compounds, which are generally organo-nitrogen compounds, including LSD, THC, heroin, cocaine, and their derivatives.

In general, the intermediate compound can be any compound with a proton affinity that is less than the proton affinity of the target compound. Preferably, the intermediate compound has a proton affinity which is greater than the proton affinity of gases in the gas mixture other than the target compound. Examples of these intermediate compounds include amines (substituted or unsubstituted; straight, branched or cyclo), such as ammonia, methyl amine, ethyl amine, propyl amine, dimethyl amine, diethyl amine, dipropyl amine and the like. Preferably, the intermediate compound is a primary amine or a secondary amine, more preferably a primary amine. In some embodiments, the intermediate compound preferably has a molecular weight such that the signal due to ionization of the intermediate compound (and its byproducts) does not interfere with signal 220.

Preconcentrator 214 can include a surface whose temperature is modulated between two temperatures. At the lower temperature (e.g., from about 25° C. to about 125° C.), the surface can condense the target compound but not certain common interfering compounds.

At the higher temperature (e.g., from about 150° C. to about 300° C.), the target compound can evaporate. By combining the temperature modulation with a corresponding modulation of gas flow, the condensable components of the sampled gas can be directed in a relatively concentrated form into spectrometer 200. Generally, preconcentrator 214 should have a relatively low thermal mass which can assist in relatively rapid heating and cooling. Examples of preconcentrator surfaces that can be used include permeable organic membranes and/or thin metal foils.

Ionizer 230 can be any ionizer capable of interacting with the intermediate compound to ionize the intermediate compound so that the ionized intermediate compound can, in turn, interact with and ionize the target compound by proton transfer. Examples of these ionizers include electron emission ionizers, such as beta particle emitting radioactive species (e.g., $^{63}$Ni), corona discharge ionizers and photon emitting sources, such as lasers or lamps. Examples of lasers and/or lamps are disclosed in U.S. Pat. No. 5,338,931 to Spangler et al.; U.S. Pat. No. 5,394,413 to Zayhowski; and J. J. Zayhowski et al., *Diode-pumped passively Q-switched picosecond microchip lasers,* Opt. Lett. 19, 1427 (1994), which are hereby incorporated by reference.

Grid 240 is generally used to modulate the extraction of ions into drift region 250. Grid 240 is usually kept at a potential that keeps the ionization region substantially field free. At a relatively short duty cycle (e.g., less than about one percent) and for a time (e.g., less than about one millisecond) that is substantially less than the total ion drift time (e.g., about 25 milliseconds), the grid is changed to a lower potential to create an electric field that extracts ions into drift region 250.

The electric field in drift region 250 is usually from about zero Volts per centimeter to about 500 Volts per centimeter (e.g., from about 150 Volts per centimeter to about 300 Volts per centimeter).

Electrode detector 260 is typically a piece of electrically conductive material (e.g., brass). When ions strike the surface of detector 260, the charge is collected as a current as a function of time and then amplified. The resulting plot of current as a function of time is commonly referred to as the ion drift spectrum.

In certain embodiments, the presence of undesired, non-ionized species in drift region 250 can reduce the sensitivity and/or selectivity of spectrometer 205 toward the target compound. To reduce the amount of these species in drift region 250, a counterflow of gas (e.g, nitrogen, argon, helium, krypton, neon, dry and/or filtered air, or a mixture thereof) enters spectrometer 205 through port 270 and exits through port 280. In some embodiments, the gas is relatively pure.

Figure 4:
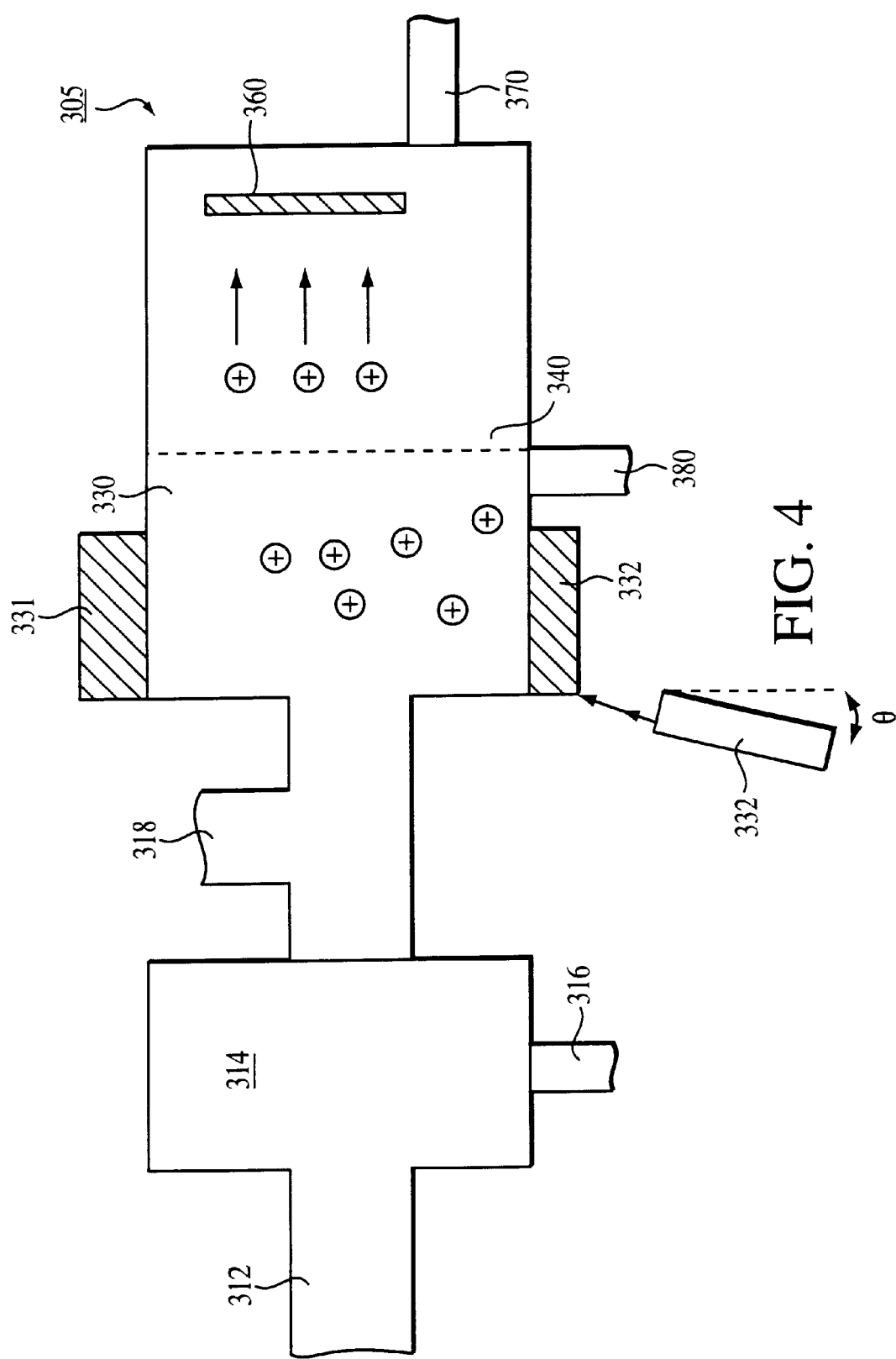
FIG. 4 is a cross-sectional view of an electron transfer ion mobility spectrometer according to another embodiment of the invention.

FIG. 4 is a cross-sectional view of an embodiment of electron transfer ion mobility spectrometer 305. A gas containing the target compound enters through port 312 and flows toward a mirror cavity 330 having mirrors 331 and 333. Prior to reaching mirror cavity 330, the gas interacts with a preconcentrator 314 which can condense relatively high boiling point species contained in the gas. The condensed, relatively high boiling point species exit through output 316. The portion of the gas that is not condensed by preconcentrator 314 is mixed with an appropriate intermediate compound which enters spectrometer 305 through port 318. The gas mixture containing the target compound and the intermediate compound enters mirror cavity 330. Photons emitted by a laser 332 also enter mirror cavity 330 at an angle θ (e.g., from about zero milliradians to about 25 milliradians) so that the photons from laser 332 bounce between mirrors 331 and 333. The photons in mirror cavity 330 interact with and ionize the intermediate compound. The ionized intermediate compound, in turn, ionizes the target compound by electron transfer (e.g., by collisions between the ionized intermediate compound and the target compound). The ionized target compound is attracted to a grid 340 and subsequently flows through a drift region 350 toward an electrode detector 360. The ion current at electrode detector 360 is measured as a function of time and output as signal 321.

Preconcentrator 314 is typically as described above with respect to preconcentrator 214.

Laser 332 should emit photons that can ionize the intermediate compound. Examples of lasers 332 include visible-ultraviolet (VUV) flash lamps and UV lasers. Examples of UV lasers include tunable UV lasers, microchip UV lasers and tunable, microchip UV lasers. Using a UV laser (e.g., a laser emitting photons having a wavelength greater than photons having VUV wavelengths) can reduce the probability that a photon will be absorbed by certain background gases (e.g., oxygen). This can increase the effective path length of the photons, which can increase the probability that a photon emitted by UV laser 332 will interact with and ionize the intermediate compound in mirror cavity 330. In embodiments in which laser 332 is a UV laser, the photons emitted by laser 332 can have a wavelength of at least about 160 nanometers (e.g., at least about 190 nanometers, at least about 250 nanometers). In certain embodiments, laser 332 is a tunable, microchip UV laser that emits photons at a wavelength of about 266 nanometers, as described in J. J. Zayhowski et al., *Diode-pumped Passively Q-switched Picosecond Microchip Lasers,* Opt. Lett. 19, 1427 (1994); and U.S. Pat. No. 5,394,413 to Zayhowski. In some embodiments, laser 332 can be operated using a pulse energy of about 12 microjoules, a pulse duration of about 270 picoseconds, a peak power of about 44 kilowatts, a maximum repetition rate of about five kilohertz, a beam diameter of about 0.2 millimeter, a peak power density of greater than about 50 megawatts per square centimeter, and/or a power supply weighing less than about five pounds.

Mirrors 331 and 333 can be made of any material capable of reflecting the photons emitted by laser 332. Examples of such materials include a glass substrate with a reflective coating (e.g., a thin metallic coating and/or a stack of dielectric layers).

Grid 340 is generally as described above with respect to grid 240.

The electric field in drift region 350 is usually from about zero Volts per centimeter to about 500 Volts per centimeter (e.g., from about 150 Volts per centimeter to about 300 Volts per centimeter).

Electrode detector 360 is generally as described above with respect to detector 260.

In some embodiments, the presence of undesired, non-ionized species in drift region 350 can reduce the detection sensitivity and/or detection selectivity of spectrometer 305 toward the target compound. To reduce the amount of these species in drift region 350, a counterflow of pure gas (e.g, nitrogen, argon, helium, krypton, neon or a mixture thereof) enters spectrometer 305 through port 370 and exits through port 380. In certain embodiments, the gas is relatively pure.

The target compound can be as described above.

In general, the intermediate compound can be any compound with an ionization potential that is greater than the ionization potential of the target compound. Examples of these intermediate compounds include aromatic compounds, such as compounds containing a benzene ring, including benzene, toluene, xylene, aniline and the like. In some embodiments, the intermediate compound preferably has a molecular weight such that the signal due to ionization of the intermediate compound (and its byproducts) does not interfere with signal 320.

Figure 5:
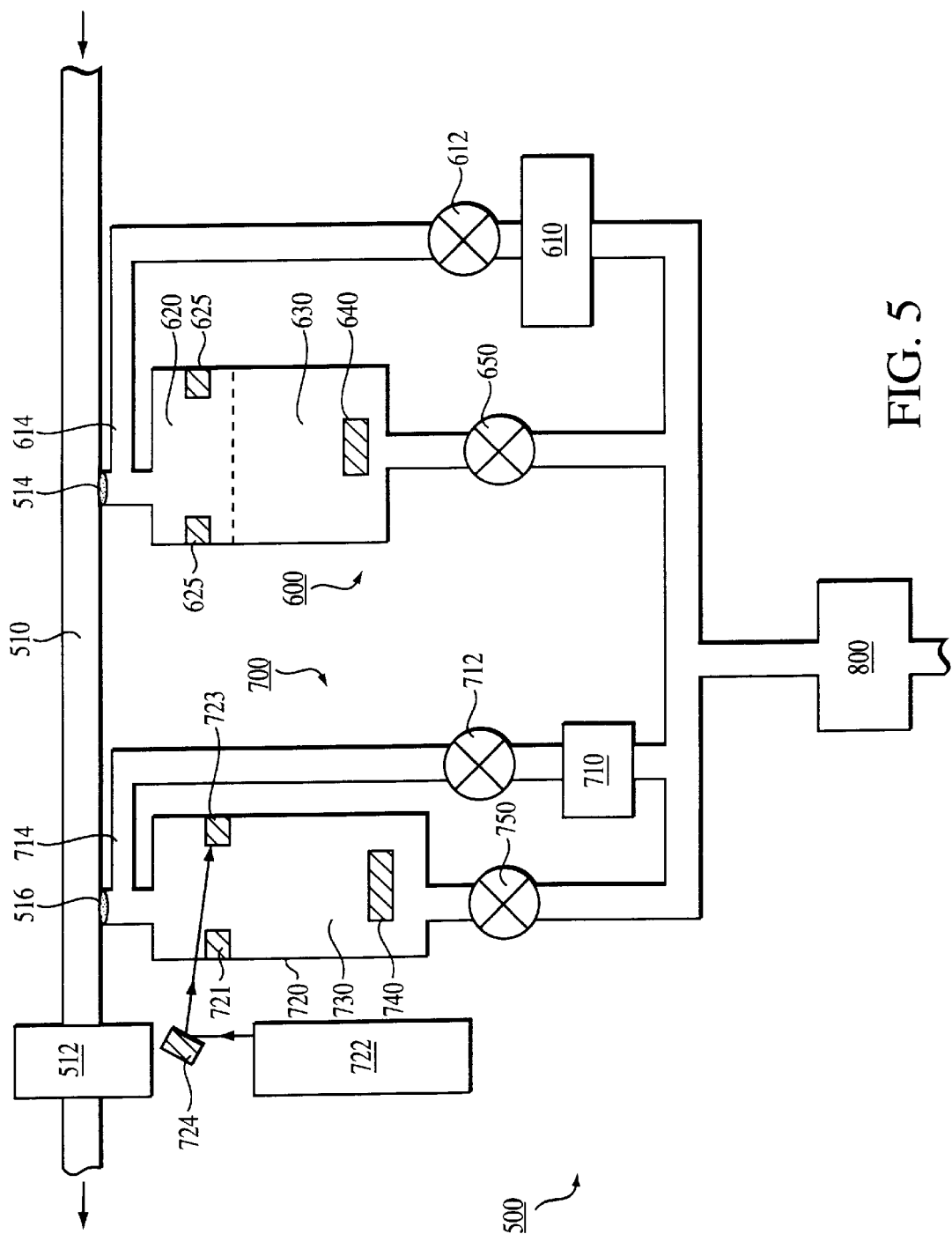
FIG. 5 is a cross-sectional view of an ion mobility spectrometer system according to an embodiment of the invention.

FIG. 5 shows an embodiment of an ion mobility spectrometer system 500 including a proton affinity ion mobility spectrometer 600 and an electron transfer ion mobility spectrometer 700 arranged so that one flow tube 510 is used to transport the target compound into spectrometers 600 and 700. A gas containing the target compound is urged through flow tube 510 by pump 512 (e.g., by applying a vacuum at the distal end of flow tube 510). As the gas flows along flow tube 510, it encounters permeable membranes 514 and 516, which allows some of the target compound to enter spectrometers 600 and 700, respectively.

Upon entering spectrometer 600, the target compound is mixed with an appropriate intermediate compound which flows from source 610 through regulator 612 to region 614. The mixture of target compound and intermediate compound then enter an ionizer region 620 having an electron source 625. The intermediate compound is ionized in ionizer region 620. The ionized intermediate compound interacts with and ionizes the target compound, and the target compound flows through a drift region 630 to an electrode detector 640. The signal from detector 640 is output to a comparison apparatus. A gas (e.g., air) flows through filter 800 and regulator 650 to drift region 630 to reduce the amount of undesired, non-ionized species in drift region 630.

Upon entering spectrometer 700, the target compound is mixed with an appropriate intermediate compound which flows from source 710 through regulator 712 to region 714. The mixture of target compound and intermediate compound then enter a mirror cavity 720 having mirrors 721 and 723. A laser 722 emits photons that bounce off a mirror 724 and enter mirror cavity 720, where the photons bounce between mirrors 721 and 723. The intermediate compound is ionized in mirror cavity 720. The ionized intermediate compound interacts with and ionizes the target compound, and the target compound flows through a drift region 730 to an electrode detector 740. The signal from detector 640 is output to a comparison apparatus. A gas (e.g., air) flows through filter 800 and regulator 750 to drift region 730 to reduce the amount of undesired, non-ionized species in drift region 730.

The following examples are illustrative in nature and not intended to be limiting.

EXAMPLE I

Apparatus and Operating Conditions

A modified Mark II spectrometer (Ion Track Systems, Wilimington, Mass.) was used in this example. The electrodes, voltages and preamp were not modified, but the $^{63}$Ni ionizer was removed and replaced with coplanar 266 nanometer dielectric mirrors spaced one centimeter apart. A stainless steel grid was placed between the mirrors and suspended approximately five millimeters away from the entrance to the drift region to provide the mechanism to inject ions into the drift region. An aluminum box surrounded the mirror/grid assembly and was attached by a 0.125 inch outer diameter fused silica-lined tube to a Hewlett Packard gas chromatograph injector. The mirrors, ion mobility spectrometer and aluminum box were all placed in a temperature controlled oven. The gas chromatograph injector was equipped with a carrier gas line to allow for introduction of the intermediate compound. A small hole in the aluminum box allowed entry of the laser beam, which was designed as described in U.S. Pat. No. 5,394,413 to Zayhowski. No attempts were made to filter the 532 nanometer second harmonic radiation from the frequency-quadrupled 266 nanometer radiation.

The laser operating conditions were as shown in Table I.

TABLE I

| Wavelength | 266 nanometers |
|---|---|
| Pulse Energy | 12 microJoules |
| Pulse Duration | 270 picoseconds |
| Peak Power | 44 kilo Watts |
| Maximum Repetition Rate | 5 kiloHerz |
| Beam Diameter | 0.2 millimeter |
| Peak Power Density | >50 MegaWatts/cm$^2$ |
| Power Supply | < five pounds |

Drift Time Measurement

The drift times of various molecular weight compounds were determined using direct ionization by the laser. This method of ionization results in little fragmentation, according to D. M. Lubman et al., *Resonance-enhanced two-photon ionization spectroscopy in plasma chromatography*, Anal. Chem. 55, 1486 (1983), which is hereby incorporated by reference.

Figure 6:
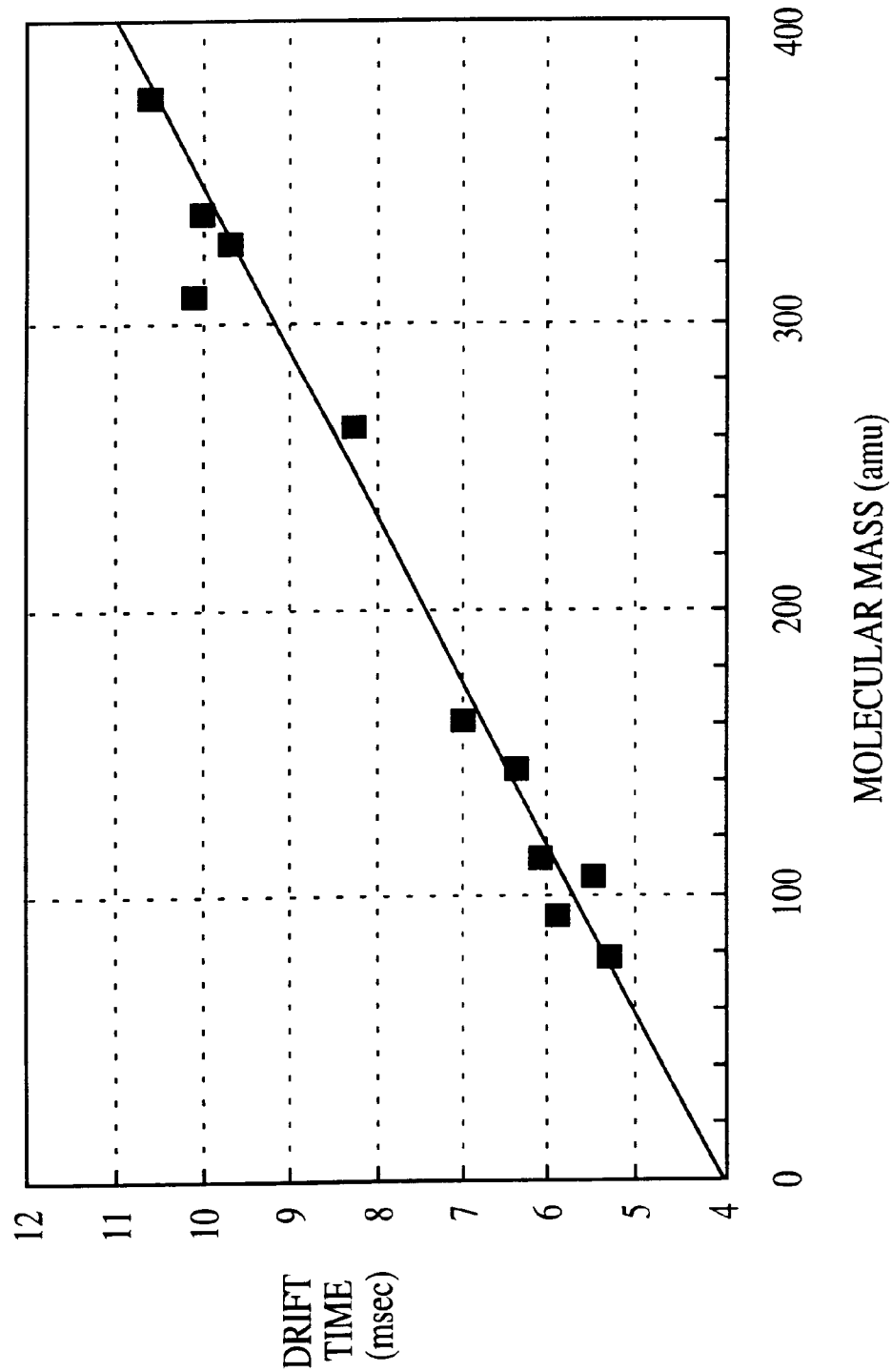
FIG. 6 shows the drift time as a function of parent molecule molecular weight for a variety of compounds detected using electron transfer ionization.

FIG. 6 shows the drift time as a function of the molecular weight of the parent molecule for a variety of compounds as detected using electron transfer ionization. Table II lists compounds from FIG. 6 in order of increasing molecular weight of the parent molecule. Ammonia was used as the intermediate compound.

TABLE II

| Benzene |
|---|
| Toluene |
| Xylene |
| Chlorobenzene |
| Methylnaphthalene |
| Nicotine |
| Cocaine |
| LSD |
| THC |
| Heroin |

The experiments were run using an oven temperature of approximately 180° C. The reduced mobilities calculated from these data are in good agreement with the values published in W. McGann et al., *A New, High Efficiency Ion Trap Mobility Detection System for Narcotics and Explosives*, Proc. SPIE 2092, 64 (1993); L. Kolatis et al., *Atmospheric Ionization Mass Spectrometry with Laser-Produced Ions*, Anal. Chem. 58, 1993 (1986); and J. W. Leonhardt et al., *Determination of Benzene, Toluene and Xylene by Means of an Ion Mobility Spectrometer Device Using Photoionization*, in Proc. Third Int. Workshop on Ion Mobility Spectrometry, J. Cross, ed., Lyndon Johnson Space Center, Houston, Report S-799, 49 (1995), which are hereby incorporated by reference.

Electron Transfer Ionization

Figure 7:
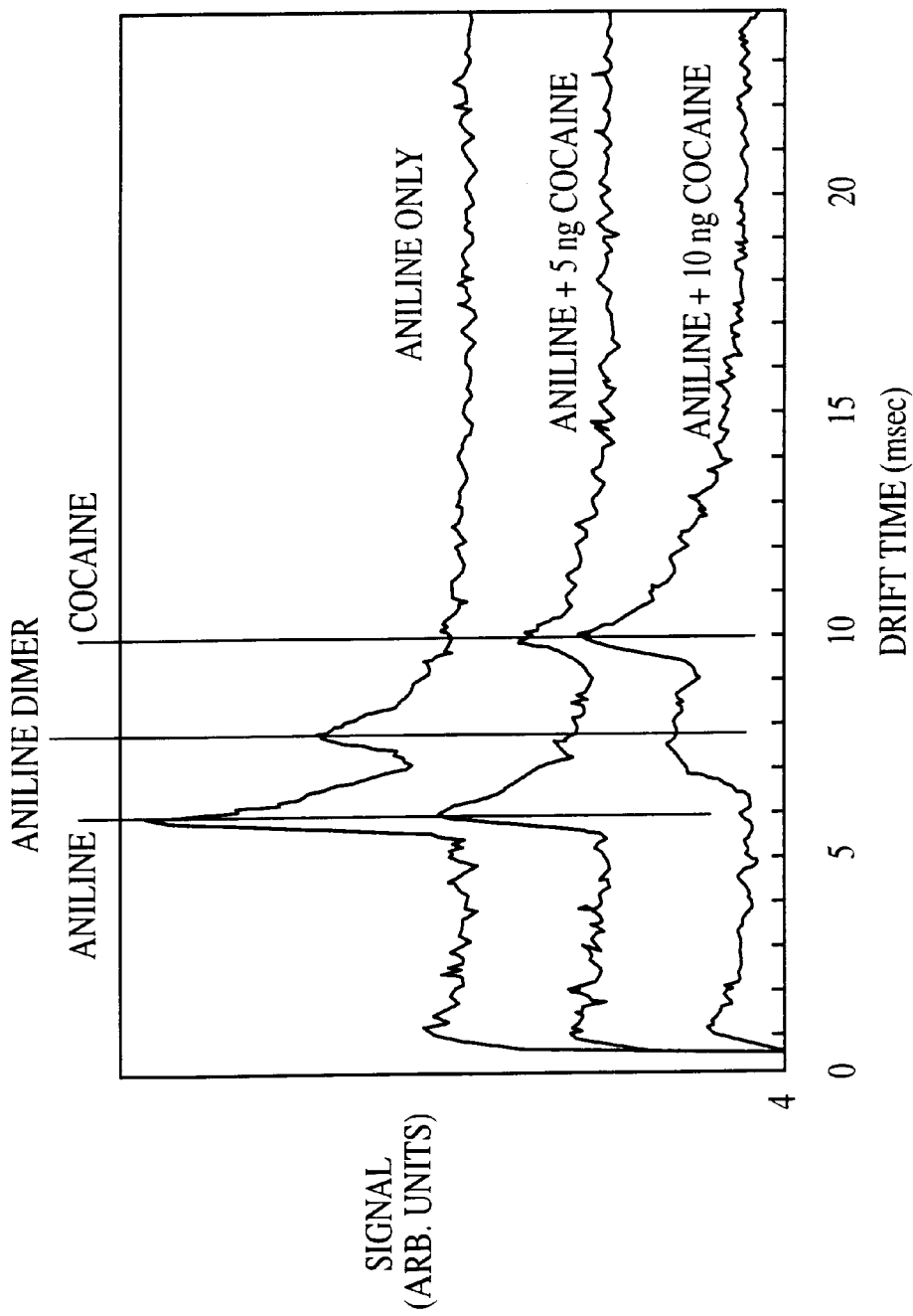
FIG. 7 shows cocaine spectra in the presence of ionized aniline.
Figure 8:
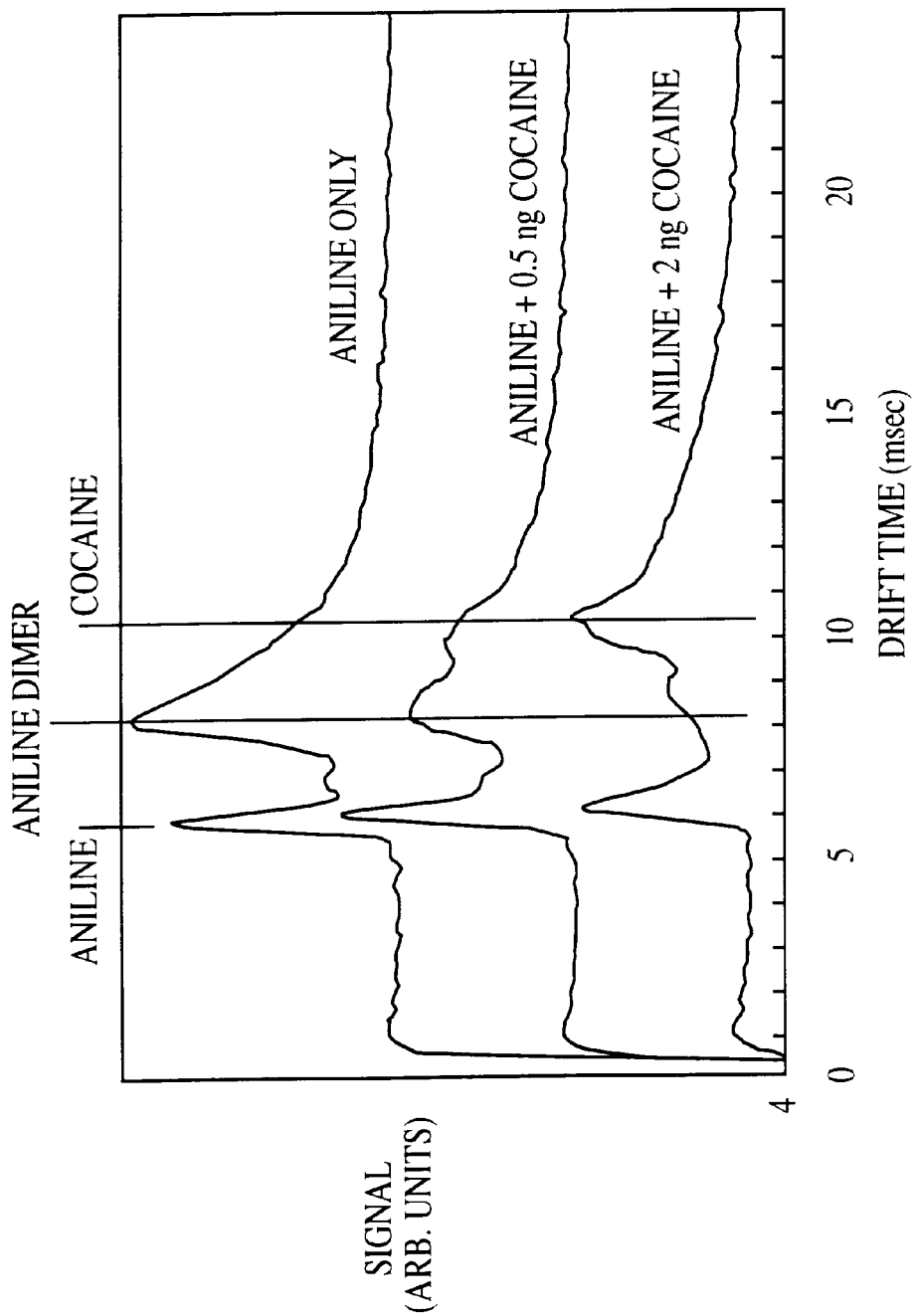
FIG. 8 shows cocaine spectra in the presence of ionized aniline.

FIG. 7 shows cocaine spectra in the presence of ionized aniline (approximately one part per million) using nitrogen as the carrier gas and a counterflow of approximately 100 standard cubic centimeters minute. FIG. 8 shows cocaine spectra in the presence of ionized aniline (approximately one part per million) using nitrogen as the carrier gas and a counterflow of approximately 50 standard cubic centimeters minute. In FIGS. 7 and 8, the injected quantities of cocaine were in the 0.5 nanogram to 10 nanogram range.

To determine the role of proton attachment during ionization, a sample of cocaine in methanol/water solution was injected (not shown in the figures). Substantially no change in the signal was observed, and substantially no low-mass ions were formed. This indicates that the predominant ionization mechanism in these experiments was electron transfer.

Detection Limits

Figure 9:
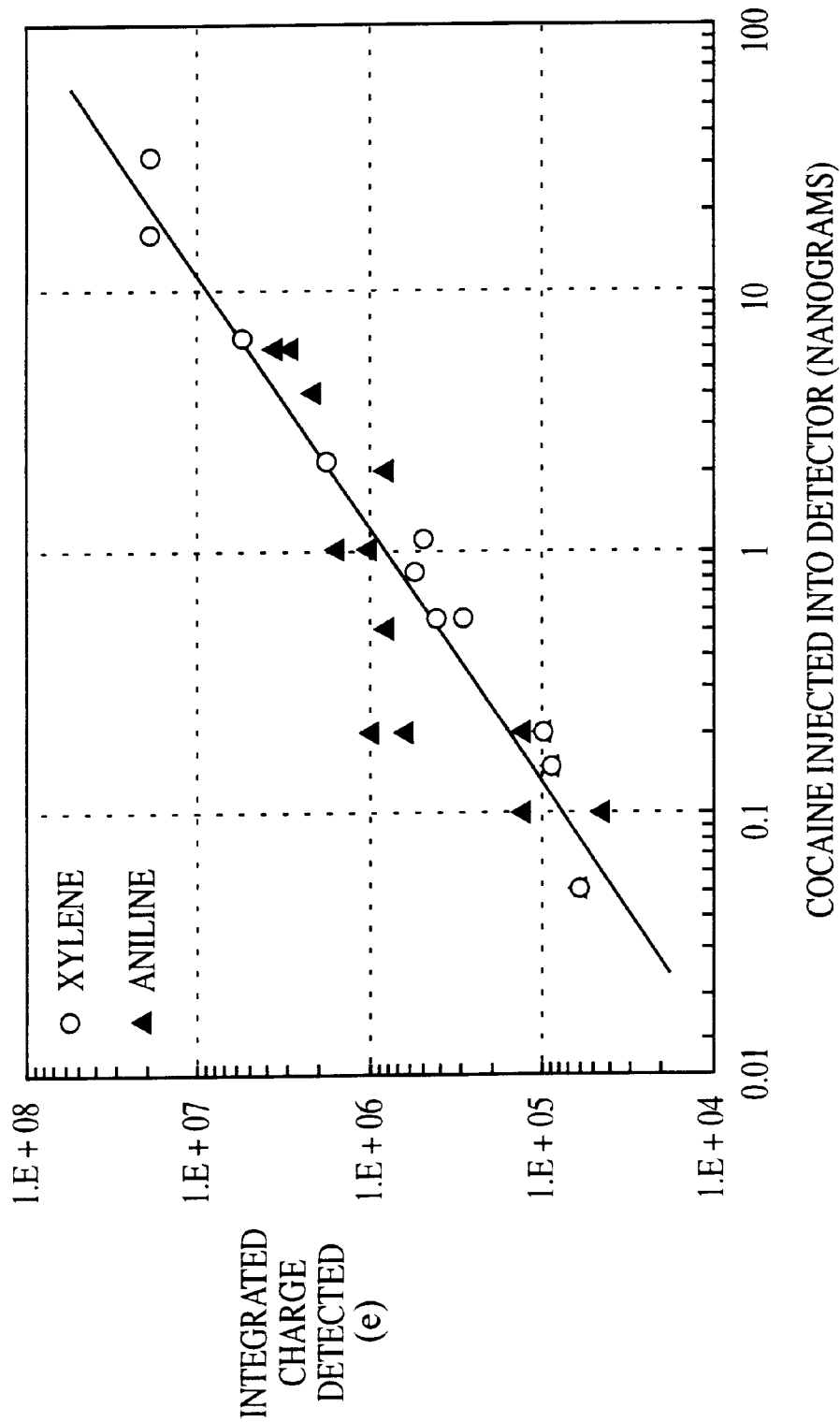
FIG. 9 shows the signal as a function of mass of cocaine injected in the presence of either xylene and aniline.

The detection limits of the experimental apparatus were determined under conditions with no counterflow. FIG. 9 shows the signal as a function of mass of cocaine injected for two intermediate compounds, xylene (a mixture of ortho, meta and para) and aniline. The data indicate that the minimum detectable quantity was about 50 picograms, and usable signals were present at about 200 picograms. Adding counterflow tended to decrease the detection limits.

Detection of Additional Compounds

In addition to cocaine, other compounds were tested using the above-described experimental set up. LSD, heroin, caffeine, nicotine, naphthalene and ethylene diamine were detected. Benzene, N-methyl pyrrolidone, toluene, methanol, isopropanol, cyclohexane, xylene, water and THC were not detected.

EXAMPLE II

Apparatus and Operating Conditions

A Mark II spectrometer (Ion Track Systems, Wilimington, Mass.) was used in the example. The spectrometer had a $^{63}$Ni ionizer. The detection limits using this type of apparatus are discussed, for example, in P. Becotte-Haigh et al., *Performance and Applications of a New Portable Detection System for Drugs and Explosives*, proceedings at the 6$^{th}$ Int. Conf. On Ion Mobility Spectrometry, August, 1997.

Drift Time Measurement

Figure 10:
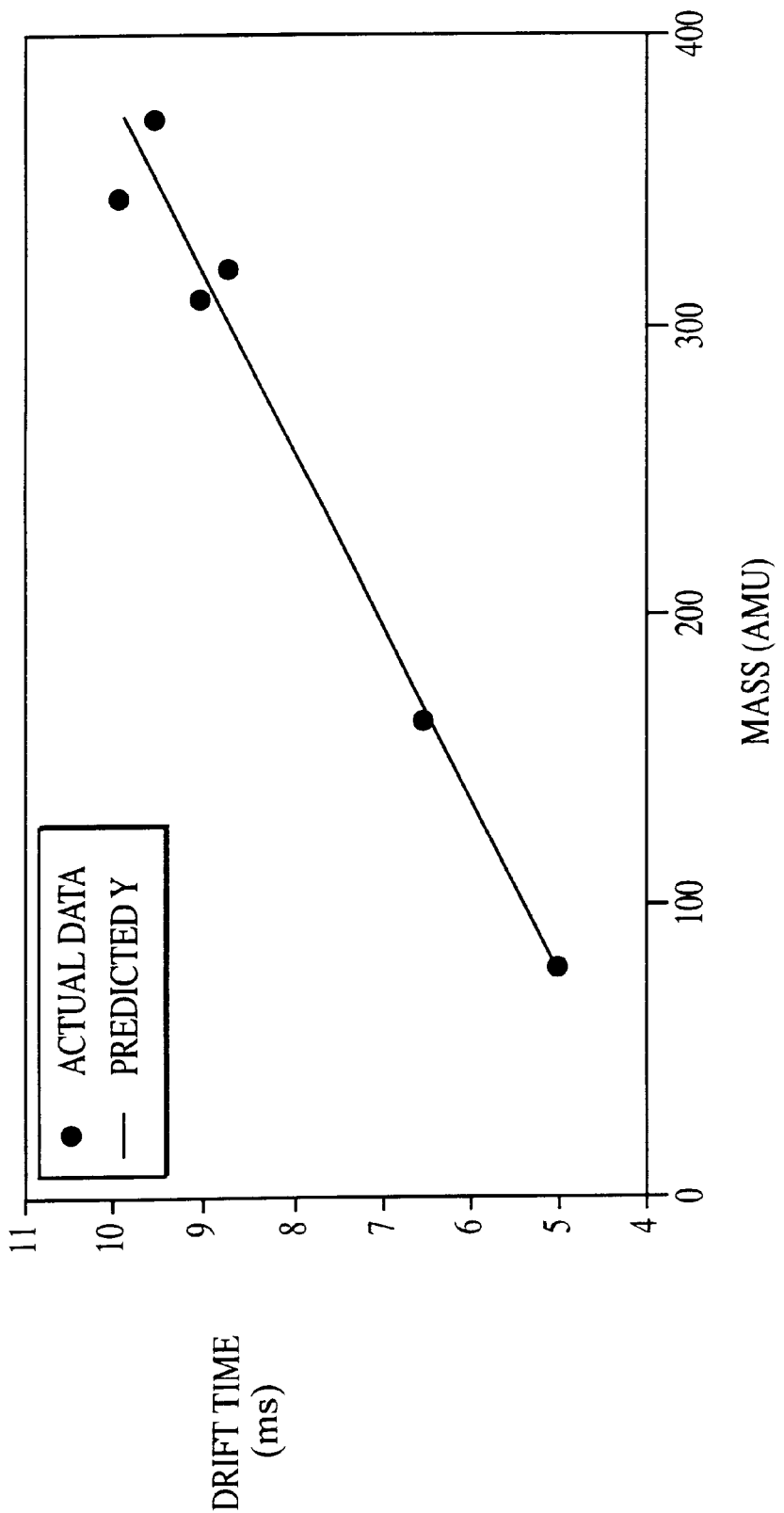
FIG. 10 shows the drift time as a function of parent molecular weight for a variety of compounds detected using proton transfer ionization.
Figure 11:
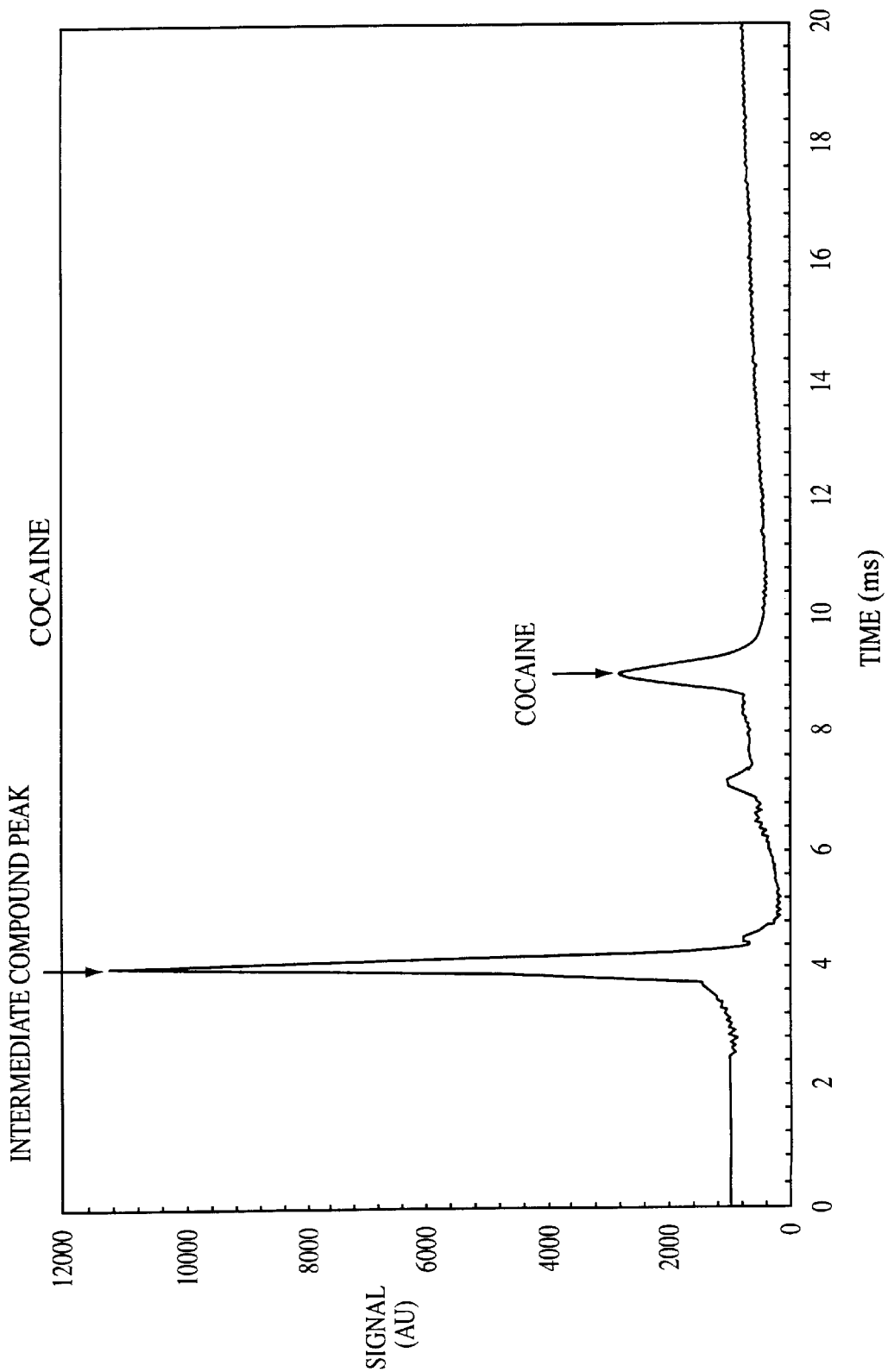
FIG. 11 shows the cocaine drift spectrum in the presence of ammonia.
Figure 12:
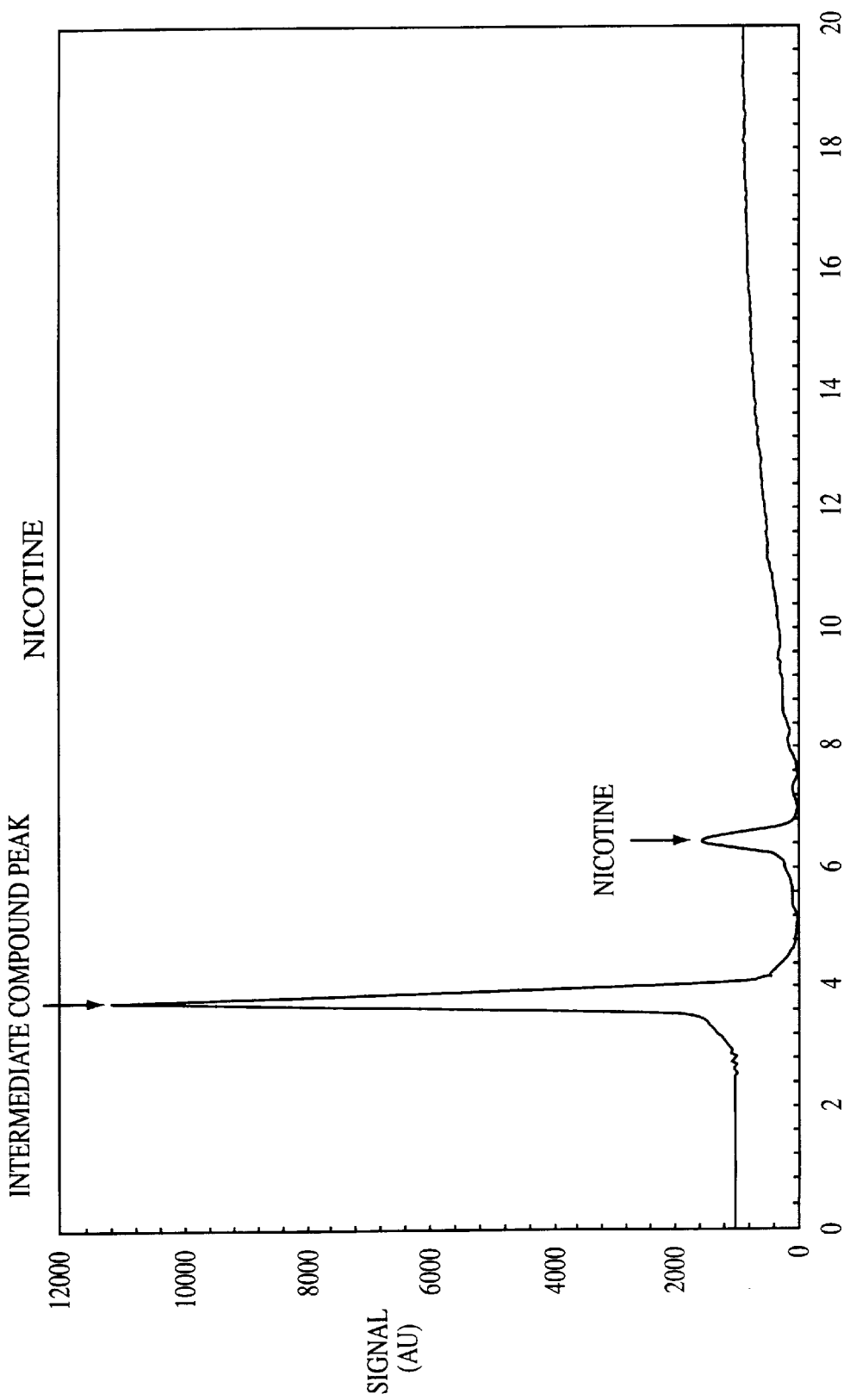
FIG. 12 shows the nicotine drift spectrum in the presence of ammonia.
Figure 13:
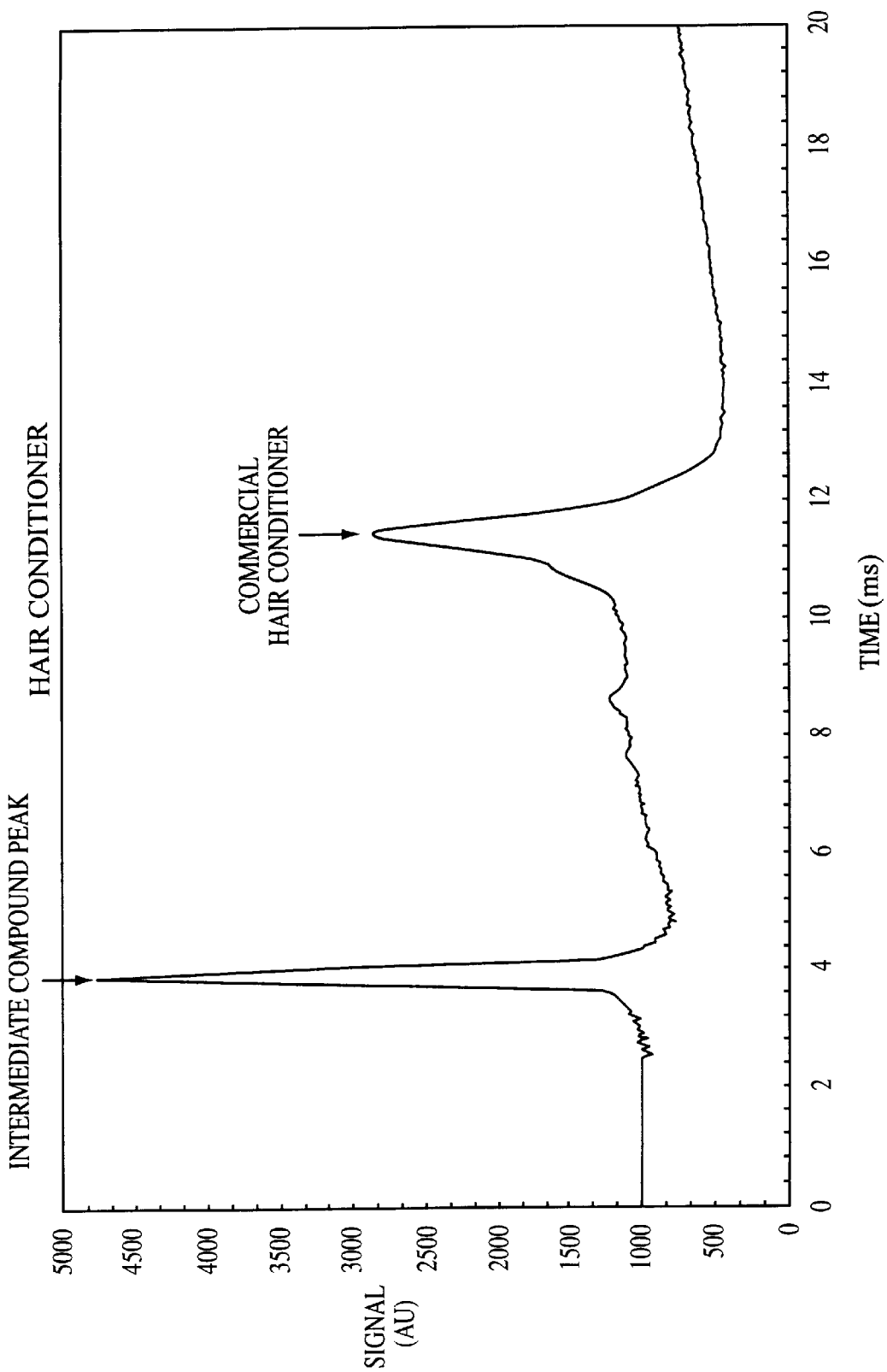
FIG. 13 shows the drift spectrum of a hair conditioner in the presence of ammonia.
Figure 14:
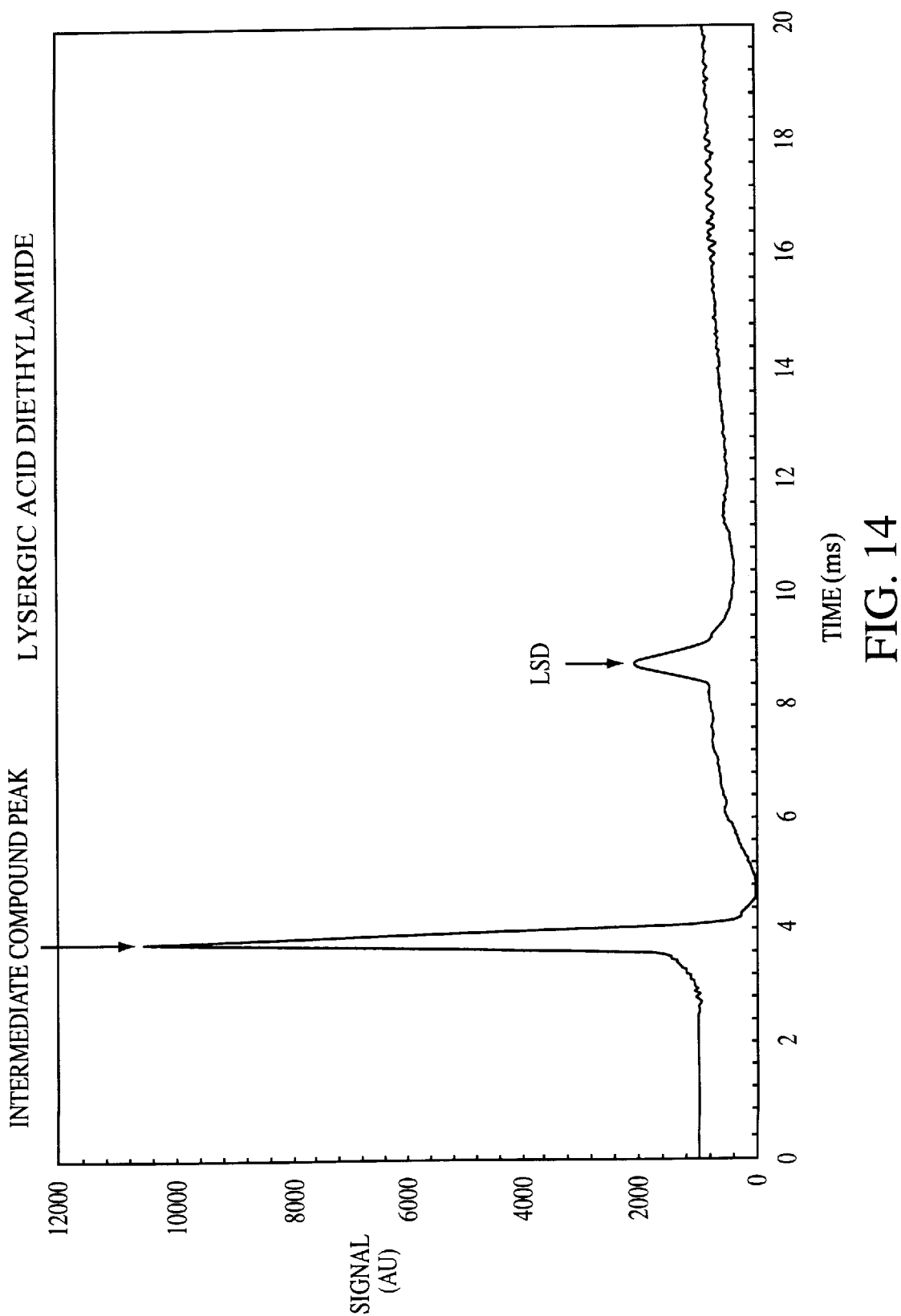
FIG. 14 shows the LSD drift spectrum in the presence of ammonia.
Figure 15:
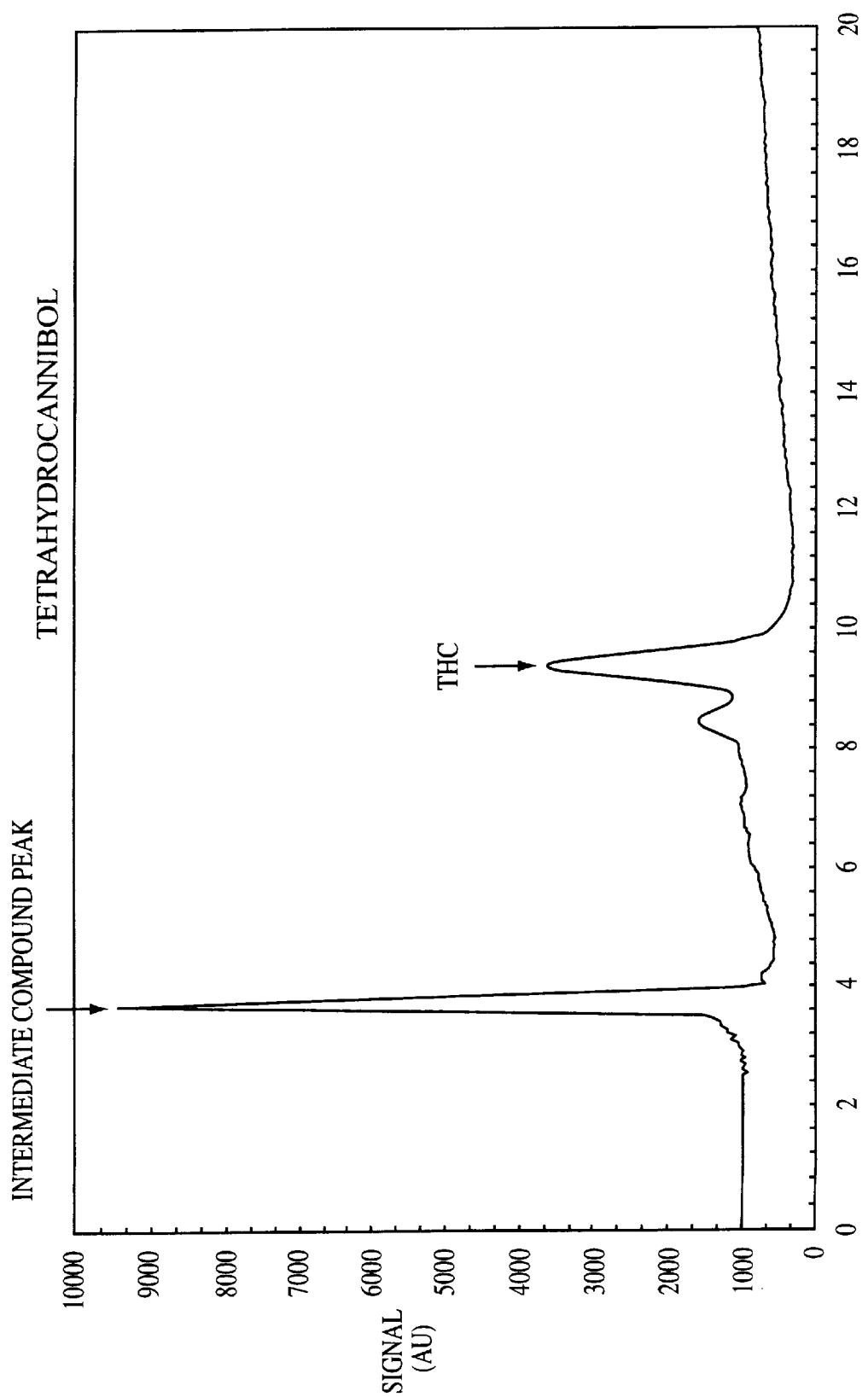
FIG. 15 shows the THC drift spectrum in the presence of ammonia.
Figure 16:
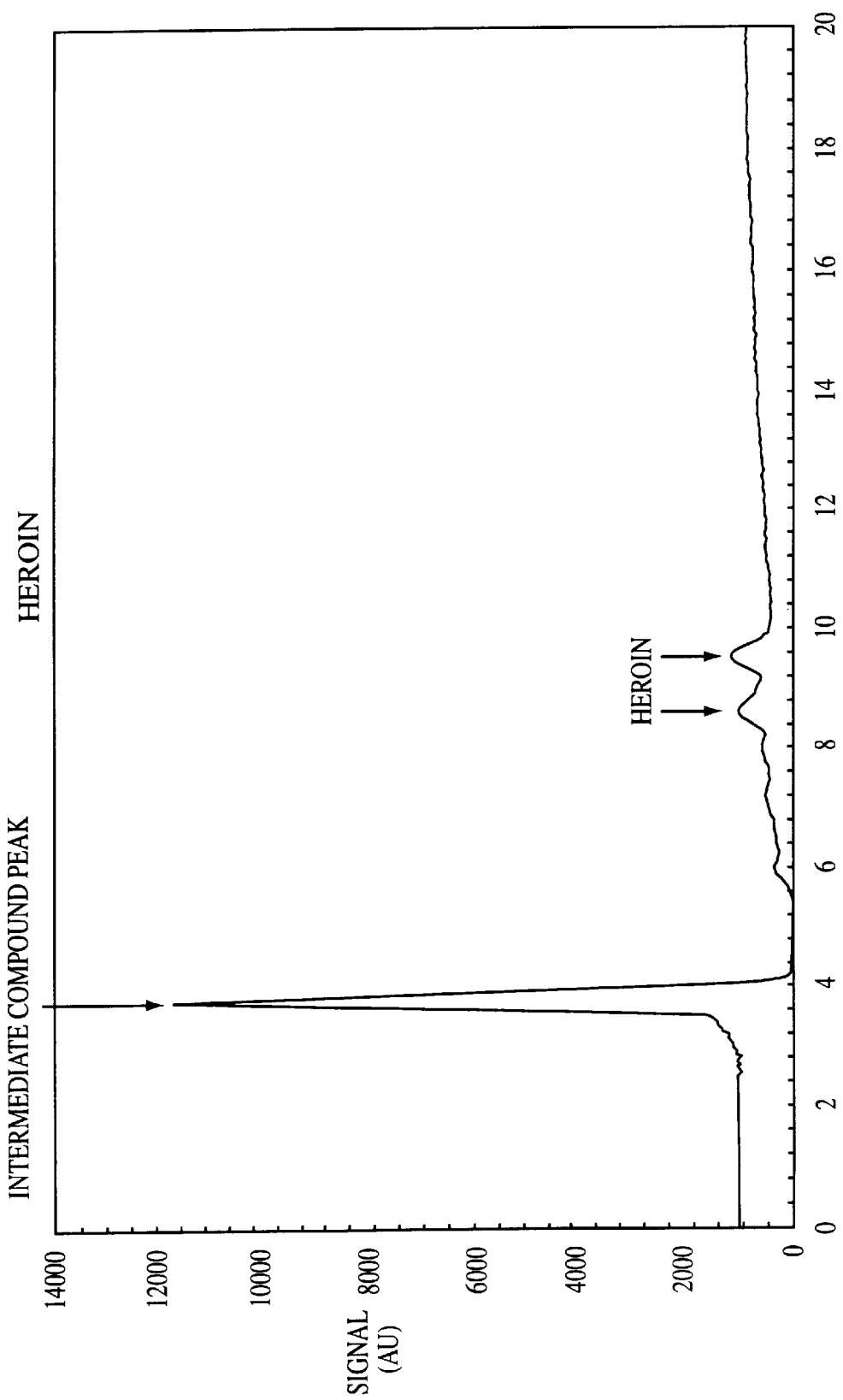
FIG. 16 shows the heroin drift spectrum in the presence of ammonia.

FIG. 10 shows the drift time as a function of the molecular weight of the parent molecule for a variety of compounds. Table III lists compounds from FIG. 10 in order of increasing molecular weight of the parent molecule as detected using proton transfer ionization. Ammonia was used as the intermediate compound.

TABLE III

| Benzene |
|---|
| Nicotine |
| Cocaine |
| LSD |
| THC |
| Heroin |

Proton Transfer Ionization

FIGS. 11–16 show spectra for cocaine, nicotine, hair conditioner (Suave), LSD, THC, and heroin, respectively. The intermediate compound was ammonia, which was present in an amount of from about 0.1 part per million to about 10 parts per million.

EXAMPLE III

The data is compared as follows.

A drift spectrum ("spectrum A") is taken of a target compound (e.g., cocaine) using an appropriate intermediate compound (e.g., aniline) and the above-described laser.

A drift spectrum ("spectrum B") is taken of the target compound (e.g., cocaine) using an appropriate intermediate compound (e.g., ammonia) and a Mark II spectrometer (Ion Track Systems, Wilmington, Mass.).

A three dimensional plot is formed plotting the signal from spectrum A on the X-axis, the signal from spectrum B on the Y-axis, and time on the Z-axis. In this plot, a data point at a given time that appears at the origin in the X-Y plane corresponds to a lack of signal in both spectra A and B. A data point at a given time that is present on the X-axis but not on the Y-axis corresponds to a lack of signal in spectrum A and a positive signal in spectrum B. A data point at a given time that is present on the Y-axis but not on the X-axis corresponds to a lack of signal in spectrum B and a positive signal in spectrum A.

The presence of a target compound in spectrum A, spectrum B, or both can be used to confirm the presence of a target compound in a sample.

While the foregoing discussion has described certain embodiments of ion mobility spectrometers and methods, the invention is not limited by these systems and methods. Various alterations and modifications can be made to the systems and methods and will be apparent to those skilled in the art. Such alterations and modifications are contemplated as being within the invention. For example, the flow of the target compound into the different ion spectrometers need not be from the same flow tube. In some embodiments, the flow the spectrometers can be arranged so that the flow of the target compound into the spectrometers is from different flow tubes.

Other embodiments are in the claims.

What is claimed is:

1. A method of detecting a target compound in a sample, comprising:
    subjecting the sample to conditions sufficient to ionize the target compound by proton transfer ionization;
    subjecting the sample to conditions sufficient to ionize the target compound by electron transfer ionization;
    detecting the proton transfer first ionized sample by ion mobility spectrometry; and
    detecting the electron transfer ionized sample by ion mobility spectrometry.
2. The method of claim 1, further comprising comparing the detection of the proton transfer ionized sample and the detection of the electron transfer ionized sample.
3. The method of claim 2, comprising determining the presence of the target compound by detection of the compound by both proton transfer ionization and electron transfer ionization.
4. The method of claim 1, comprising obtaining the sample by vapor collection.
5. The method of claim 1, wherein the target compound has a proton affinity of about 7.5 eV or greater and an ionization potential of about 10 eV or less.
6. The method of claim 1, wherein the target compound has a proton affinity of from about 9 eV to about 12 eV and an ionization potential of from about 5 eV to about 8 eV.
7. The method of claim 1, wherein the target compound comprises an organo- nitrogen compound.
8. The method of claim 1, wherein the target compound is selected from the group consisting of LSD, heroin, THC, cocaine, or their derivatives.
9. The method of claim 1, wherein the proton transfer ionization includes forming a first ionized intermediate compound capable of transferring a proton from the first ionized intermediate compound to the target compound.
10. The method of claim 9, wherein the electron transfer ionization includes forming a second ionized intermediate compound capable of transferring an electron from the second ionized intermediate compound to the target compound.
11. The method of claim 1, wherein the electron transfer ionization includes forming a second ionized intermediate compound capable of transferring an electron from the second ionized intermediate compound to the target compound.
12. The method of claim 10, comprising selecting a first intermediate capable of ionizing a first set of compounds including the target compound and other known compounds, and a second intermediate capable of ionizing a second set of compounds including the target compound and other known compounds different than the first set.
13. The method of claim 9, wherein the first intermediate compound comprises an amine.
14. The method of claim 9, wherein the first intermediate compound comprises a primary amine.
15. The method of claims 10 or 11, wherein the second intermediate compound comprises an aromatic compound.
16. The method of claims 10 or 11, wherein the second intermediate compound comprises a compound containing a benzene ring.
17. The method of claim 1, wherein the proton transfer and electron transfer ionizations are detected simultaneously.
18. The method of claim 1, wherein the proton transfer and electron transfer ionizations are detected in series.
19. A system capable of detecting a target compound, comprising:
    a proton transfer ionization source capable of ionizing a first intermediate compound to form a first ionized intermediate compound, the first intermediate compound having a lower proton affinity than the target compound; and
    an electron transfer ionization source capable of ionizing a second intermediate compound to form a second ionized intermediate compound, the second intermediate compound having a higher ionization potential than the target compound; and
    a detector capable of detecting the target compound after ionization by electron transfer or proton transfer.
20. The system of claim 19, wherein the detector is an ion mobility spectrometer.
21. The system of claim 20, wherein the detector comprises two ion mobility spectrometers operating in parallel.
22. The system of claim 20, wherein the detector is a single ion mobility spectrometer for alternately detecting the proton transfer source and the electron transfer source.
23. The system of claim 19, further comprising a comparison apparatus in electrical communication with the detector, the comparison apparatus being capable of comparing a first signal from ionization by proton transfer ionization with a second signal from ionization by electron transfer ionization.
24. The system of claim 23, wherein the comparison apparatus is capable of determining the presence of the target compound by detection of the compound in both the first and second signals.
25. The system of claim 19, wherein the first ionization source is capable of emitting electrons capable of ionizing the first intermediate compound to form the first ionized intermediate compound.
26. The system of claim 19, wherein the second ionization source comprises a laser.
27. The system of claim 19, wherein the second ionization source comprises a laser that is capable of emitting photons having a wavelength of at least about 190 nanometers.
28. The system of claim 19, wherein the second ionization source comprises a microchip UV laser.
29. The system of claim 19, wherein the second ionization source comprises a tunable laser.
30. The system of claim 19, wherein the target compound has a proton affinity of about 7.5 eV or greater and an ionization potential of about 10 eV or less.
31. The system of claim 19, wherein the target compound has a proton affinity of from about 9 eV to about 12 eV and an ionization potential of from about 5 eV to about 8 eV.
32. The method of claim 19, wherein the target compound is selected from the group consisting of LSD, heroin, THC, cocaine, or their derivatives.

33. A system for detecting a target compound in a sample, comprising:

a sample inlet;

a first ionization source capable of emitting electrons capable of ionizing a first intermediate compound to form a first ionized intermediate compound, the first intermediate compound having a lower proton affinity than the target compound and the target compound having a proton affinity of about 7.5 eV or greater; and a laser capable of emitting photons capable of ionizing a second intermediate compound to form a second ionized intermediate compound, an ionization potential of the second intermediate compound being greater than an ionization potential of the target compound and the target compound having an ionization potential of about 10 eV or less;

a detector comprising an ion mobility spectrometer capable of detecting the first ionized target compound and the second ionized target compound; and a comparison apparatus in electrical communication with the detector so that the comparison apparatus can compare a first signal corresponding to the first ionized target compound and a second signal corresponding to the second ionized target compound.

34. The system of claim 33, wherein the photons have a wavelength of at least about 190 nanometers.

35. The system of claim 33, wherein the laser comprises a UV microchip laser.

36. The system of claim 33, wherein the laser comprises a tunable laser.

37. The system of claim 33, wherein the detector comprises two ion mobility spectrometers operating in parallel.

* * * * *